US008802384B2

(12) United States Patent
Arao et al.

(10) Patent No.: US 8,802,384 B2
(45) Date of Patent: Aug. 12, 2014

(54) METHOD OR SYSTEM USING BIOMARKERS FOR THE MONITORING OF A TREATMENT

(75) Inventors: Tokuzo Arao, Osaka (JP); Kanae Kudo, Osaka (JP); Kazuhiko Nakagawa, Osaka-Sayama (JP); Kazuto Nishio, Osaka (JP)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 559 days.

(21) Appl. No.: 12/720,663

(22) Filed: Mar. 9, 2010

(65) Prior Publication Data

US 2010/0233705 A1    Sep. 16, 2010

(30) Foreign Application Priority Data

Mar. 12, 2009  (EP) .................................... 09154964

(51) Int. Cl.
*G01N 33/53*  (2006.01)
*G01N 33/574*  (2006.01)

(52) U.S. Cl.
USPC ............................ 435/7.24; 435/7.2; 435/7.23

(58) Field of Classification Search
None
See application file for complete search history.

(56) References Cited

U.S. PATENT DOCUMENTS

| 6,762,180 | B1 * | 7/2004 | Roth et al. ................. 514/228.2 |
| 7,119,093 | B2 * | 10/2006 | Roth et al. ................. 514/254.09 |
| 7,846,936 | B2 * | 12/2010 | Hilberg et al. ............ 514/254.09 |
| 7,989,474 | B2 | 8/2011 | Roth et al. |
| 2006/0142373 | A1 | 6/2006 | Park et al. |
| 2009/0318471 | A1 | 12/2009 | Sieger et al. |

FOREIGN PATENT DOCUMENTS

| CA | 2387013 A1 | 4/2001 |
| WO | 0127081 A1 | 4/2001 |
| WO | 2004/013099 A1 | 2/2004 |
| WO | 2004017948 A2 | 3/2004 |
| WO | 2004096224 A2 | 11/2004 |
| WO | 2006067165 A2 | 6/2006 |
| WO | 2007045996 A1 | 4/2007 |
| WO | 2007121464 A2 | 10/2007 |
| WO | 2007/141283 A2 | 12/2007 |
| WO | 2008128008 A2 | 10/2008 |

OTHER PUBLICATIONS

Bertolini et al., Nature Reviews. Cancer 6(11): 835-838, Nov. 2006.*
Vroling et al., Increased numbers of small circulatingendothelial cells in renal cell cancer patients treated with sunitinib, Angiogenesis, Kluwer Academic Publishers, DO, vol. 12, No. 1, Feb. 11, 2009, pp. 69-79.
Roth et al., Design, synthesis, and evaluation of indolinones as triple angiokinase inhibitors and the discovery of a highly specific, Journal of Medicinal Chemistry, vol. 52, No. 14, Jul. 2009, pp. 4466-4480.
International Search Report, Form PCT/ISA/210, for PCT Application PCT/EP2010/053063, date of mailing Jun. 6, 2010.
Zhu et al., Exploratory Analysis of Early Toxicity of Sunitinib in Advanced Hepatocellular Hepatcellular Carcinoma Patients: Kinetics and Potential Biomarker Value, Clinical Cancer Research, 2011, vol. 17, No. 4, pp. 918-927.
Roskoski et al., Sunitinib: A VEGF and PDGF receptor protein kinase and angiogenesis inhibitor, Biochemical and Biophysical Research Communications, 2007, vol. 356, No. 2, pp. 323-328.
Hilberg et al., BIBF 1120: Triple Angiokinase Inhibitor with Sustained Receptor Blockade and Good Antitumor Efficacy, Cancer Research, 2008, vol. 68, No. 12, pp. 4774-4782.
Cascone et al., Stable interaction between a5B1 integrin and Tie2 tyrosine kinase receptor regulates endothelail cell response to Ang-1, Journal of Cell Biology, 2005, vol. 170, No. 6, pp. 993-1004.

* cited by examiner

*Primary Examiner* — Daniel C Gamett
(74) *Attorney, Agent, or Firm* — Michael P. Morris; Alan R. Stempel

(57) ABSTRACT

The present invention relates to biomarkers to monitor the activity of the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone or a pharmaceutically acceptable salt thereof, and especially its monoethanesulphonate salt form, when used alone or optionally in combination with further pharmaceutically active ingredients and/or further treatments, such as for example radiotherapy.

9 Claims, 5 Drawing Sheets

METHOD OR SYSTEM USING BIOMARKERS FOR THE MONITORING OF A TREATMENT

Figure 1:
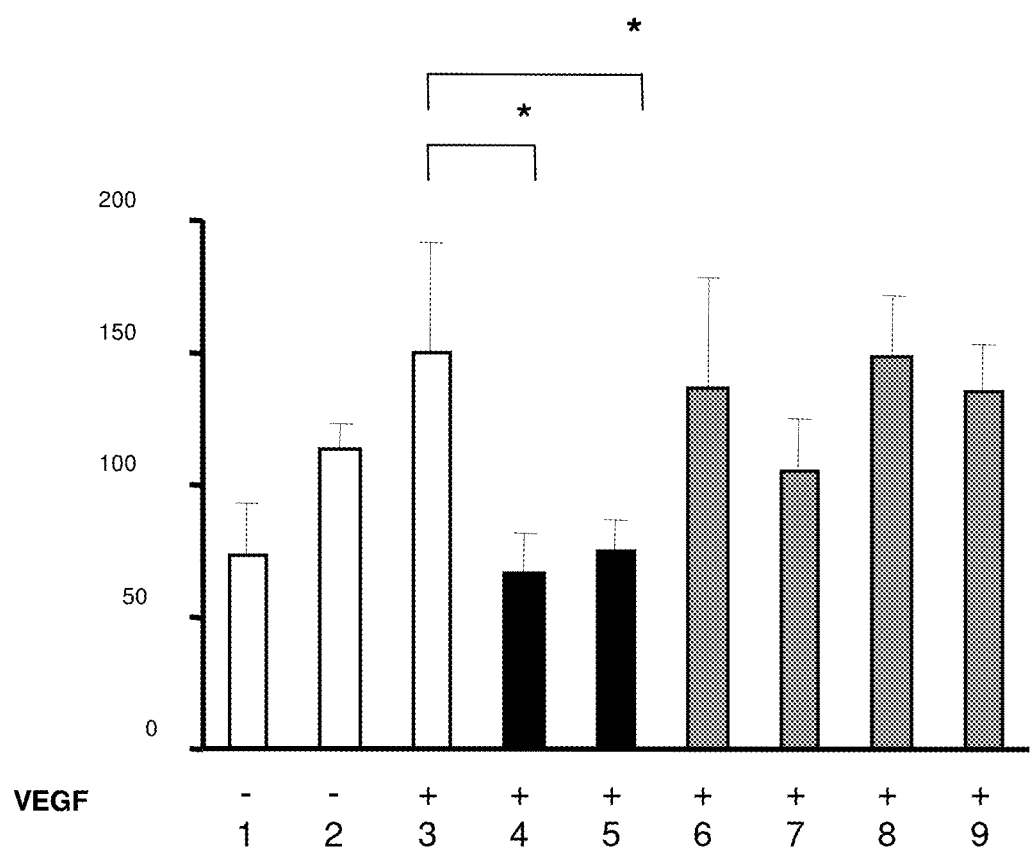

The present invention relates to the field of medicine, and especially to biomarkers of the activity of a specific compound and to the monitoring of a treatment with said compound.

The present invention relates more specifically to biomarkers to monitor the activity of the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone or a pharmaceutically acceptable salt thereof, and especially its monoethanesulphonate salt form, when used alone or optionally in combination with further pharmaceutically active ingredients and/or further treatments, such as for example radiotherapy.

BACKGROUND TO THE INVENTION

Recent advances in the knowledge of molecular processes in an organism and techniques to study these processes have resulted in improved methods and systems of typing and treating diseases. Research is being carried out in many fields in order to provide and/or improve methods for the treatment of diseases as well as providing and/or improving methods and systems for monitoring the effects of treatments.

The compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone is an innovative active ingredient having valuable pharmacological properties, especially for the treatment of oncological diseases, immunologic diseases or pathological conditions involving an immunologic component, or fibrotic diseases.

The chemical structure of this compound is depicted below as Formula A.

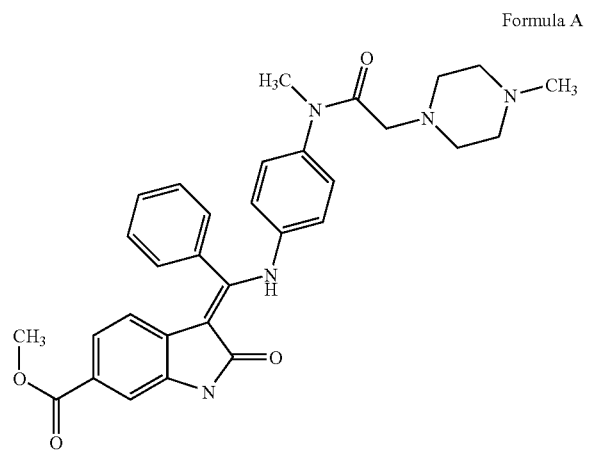 [SMILES: COC(=O)c1ccc2c(c1)NC(=O)/C2=C(\Nc1ccc(N(C)C(=O)CN2CCN(C)CC2)cc1)c1ccccc1]

Formula A

The base form of this compound is described in WO 01/27081, the monoethanesulphonate salt form is described in WO 2004/013099 and various further salt forms are presented in WO 2007/141283. The use of this molecule for the treatment of immunologic diseases or pathological conditions involving an immunologic component is being described in WO 2004/017948, the use for the treatment of ontological diseases is being described in WO 2004/096224 and the use for the treatment of fibrotic diseases is being described in WO 2006/067165.

The monoethanesulphonate salt form of this compound presents properties which makes this salt form especially suitable for development as medicament. The chemical structure of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate is depicted below as Formula A1.

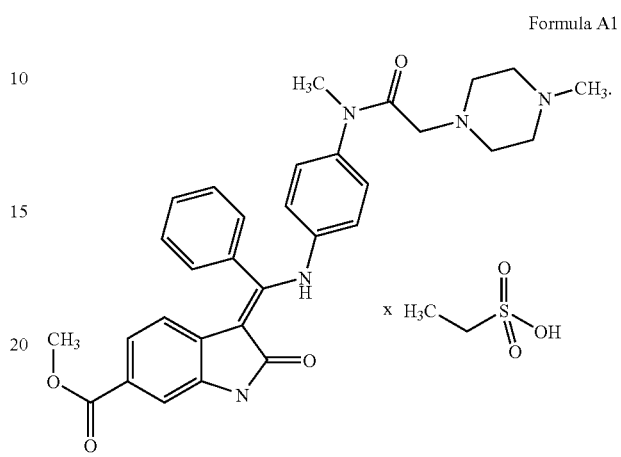

Formula A1

Preclinical studies have shown that this compound is a highly potent, orally bioavailable inhibitor of vascular endothelial growth factor receptors (VEGFRs), platelet-derived growth factor receptors (PDGFRs) and fibroblast growth factor receptors (FGFRs), that suppresses tumor growth through mechanisms inhibiting tumor neovascularization. It has further been shown that this compound inhibits signalling in endothelial- and smooth muscle cells and pericytes, and reduces tumor vessel density.

Furthermore, this compound shows in vivo anti-tumor efficacy in all models tested so far at well tolerated doses. The following Table 1 shows the results of the in vivo anti-tumor efficacy testing in xenograft models and in a syngeneic rat tumor model.

TABLE 1

| Cancer | Model | Efficacy |
|---|---|---|
| Colorectal | HT-29 | T/C 16% @ 100 mg/kg/d |
|  | HT-29 large tumors | tumor volume reduction |
| Glioblastoma | GS-9L syngeneic rat | T/C 32% @ 50 mg/kg/d |
| Head and neck | FaDu | T/C 11% @ 100 mg/kg/d |
| Lung (non-small-cell) | NCI-H460 | T/C 54% @ 25 mg/kg/d |
|  | Calu-6 | T/C 24% @ 50 mg/kg/d |
| Ovarian | SKOV3 | T/C 19% @ 50 mg/kg/d |
| Prostate (hormone-dependent) | PAC-120 | T/C 34% @ 100 mg/kg/d |
| Renal | Caki-1 | T/C 13% @ 100 mg/kg/d |
| Pancreas (murine transgenic) | Rip-Tag | interference with tumor formation |

T/C represents the reduction of tumor size in % of the control

This compound is thus for example suitable for the treatment of diseases in which angiogenesis or the proliferation of cells is involved.

This compound is further suitable for the treatment of fibrotic diseases, as described in WO 2006/067165.

Despite much research aiming at developing methods for diagnosis and screening, there remains a need for efficient methods and systems for the monitoring of treatment. Monitoring is not always possible or requires complicated, expensive and/or time-consuming procedures which are often inconvenient for a patient, such as obtaining samples, for instance biopsy samples, from a patient and studying these samples in a laboratory. Radiological analysis of tumor cells is only possible weeks after start of tumor therapy.

Thus, in accordance with WO 2008/127528, methods and procedures are provided to monitor response or determine sensitivity in patients to allow the identification of individualized genetic profiles which will aid in treating diseases and disorders.

In accordance with WO 2008/134526, bladder cancer may be detected by screening for the presence of elevated levels of identified biomarkers in urine samples. This document further describes a method for the diagnosis, prognosis, and monitoring of bladder cancer, such as early or late stage bladder cancer, by detecting in a urine sample from a subject at least one biomarker for bladder cancer identified herein, such as alpha-1B-glycoprotein, haptoglobin, sero transferrin, or alpha-1-antitrypsin. The biomarkers may be detected and, optionally, measured using an agent that detects or binds to the biomarker protein or an agent that detects or binds to encoding nucleic acids, such as antibodies specifically reactive with the biomarker protein or a portion thereof.

Thus, the expression amount of certain cell surface molecules have already been proposed as an indication of a disease or of a treatment thereof.

In accordance with WO 2005/083123, the amount of an expression product of AC133 in a sample from an individual, i.e. the amount of the protein or of its mRNA, is indicative for a disease or for the treatment thereof. This reference further states that the expression of AC133 in untreated cancer patients is significantly higher compared to healthy individuals. There is also shown in the examples that AC133 expression significantly drops when various tumor patients are treated, while the total number of circulating endothelial cells remains essentially the same during the same treatment. In essence, this reference further states that the number of circulating endothelial cells is not always indicative for the status of an individual, while the total amount of AC133 expression product is indicative for said status. Similarly, WO 2004/019864 describes the use of quantitative RT-PCR to identify AC133 as a marker and to diagnose and monitor angiogenesis.

However, no method or system using biomarkers for monitoring the treatment of an individual with the above-mentioned active ingredient 3-Z-[1-(4-(N-((4-methyl-piperazin-1-yl)-methylcarbonyl)-N-methyl-amino)-anilino)-1-phenyl-methylene]-6-methoxycarbonyl-2-indolinone or a pharmaceutically acceptable salt thereof, and especially its monoethanesulphonate salt form, when used alone or optionally in combination with further pharmaceutically active ingredients and/or further treatments, such as for example radiotherapy, has been so far described or suggested. No such method or system may also be predicted from the prior art.

SUMMARY OF THE INVENTION

The aim of the present invention is to provide a method or a system using biomarkers for monitoring the treatment of an individual with the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone or a pharmaceutically acceptable salt thereof, and especially its monoethanesulphonate salt form, when used alone or optionally in combination with further pharmaceutically active ingredients and/or further treatments, such as for example radiotherapy.

It is thus an object of the present invention to provide a method or system for the monitoring of the treatment of an individual with the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone or a pharmaceutically acceptable salt thereof, preferably the monoethanesulphonate salt form, said method comprising determining whether a sample from said individual comprises a biomarker in an amount that is indicative for said treatment.

A further object of the present invention is the above method or system, wherein the biomarker indicates a change in expression or state of a protein or in the amount of specific cells that correlates with the risk or progression of a disease or with the susceptibility of the disease to a given treatment.

In a further embodiment in accordance with the present invention, the biomarker is a pharmacodynamic biomarker.

In a further embodiment in accordance with the present invention, monitoring of the treatment means any one of: monitoring the extent of the response, monitoring the duration of response, monitoring the response rate, monitoring the stabilisation rate, monitoring the duration of stabilisation, monitoring the time to disease progression, monitoring the progression free survival or monitoring the overall survival, in particular without detriment to the duration of the response, but with fewer and/or less troublesome side-effects.

A further object of the present invention is the above method or system, wherein said amount is quantified.

A further object of the present invention is the above method and system comprising comparing said amount with a reference value.

A further object of the present invention is the above method or system, comprising comparing said amount of said expression product or specific cells with an amount of said expression product or specific cells present in a sample that was obtained from said individual before said treatment.

In a further embodiment, several samples from said individual are obtained at different time points after initiation of treatment. This enables monitoring the course of treatment during a prolonged period. It can for instance be determined whether the amount of the biomarker remains indicative for said disease or the treatment thereof. This is for instance useful for establishing appropriate treatment schedules, dosage and type on a patient per patient basis. Furthermore it can be determined whether continuation of treatment at a given time point is appropriate.

A further object of the present invention is the above method or system, wherein said sample is obtained within a month of initiation of said treatment.

A further object of the present invention is the above method or system, wherein said sample is obtained within a week of initiation of said treatment.

A further object of the present invention is the above method or system, wherein said sample is obtained within two days of initiation of said treatment.

A further object of the present invention is the above method or system, wherein said biomarker comprises cells presenting some specific cell surface antigens.

A further object of the present invention is the above method or system, wherein the sample is a blood sample.

A further object of the present invention is the above method or system, wherein said biomarker is the phosphotyrosine level of endothelial cells.

A further object of the present invention is the above method or system, wherein said biomarker is the number of VEGFR2$^+$CD45$^{dim}$pY$^+$ cells.

A further object of the present invention is the above method or system, wherein said biomarker is the number of VEGFR2$^+$pY$^+$ cells.

A further object of the present invention is the above method or system, wherein said biomarker is selected from the number of CD34$^+$CD45$^{dim}$CD133$^+$CD117$^-$ cells, the number of CD34$^+$CD45$^{dim}$ CD133$^-$CD117$^+$ cells, the number of CD34$^+$CD45$^{dim}$CD133$^+$ cells and the number of CD34$^+$CD45$^{dim}$CD117$^+$ cells.

A further object of the present invention is the above method or system, wherein said biomarker is the number of CD34$^+$CD45$^{dim}$CD133$^+$CD117$^+$ cells.

A further object of the present invention is the above method or system, wherein the decrease of phospho-tyrosine levels of endothelial cells using flow cytometry in a sample from said individual is indicative for the treatment.

A further object of the present invention is the above method or system, wherein the decrease of VEGFR2$^+$CD45$^{dim}$pY$^+$ cells using flow cytometry from a blood sample from said individual is indicative for the treatment.

A further object of the present invention is the above method or system, wherein the decrease of VEGFR2$^+$pY$^+$ cells using flow cytometry from a blood sample from said individual is indicative for the treatment.

A further object of the present invention is the above method or system, wherein an increase of the percentage of CD34$^+$CD45$^{dim}$CD133$^+$CD117$^-$ cells as measured after treatment, for example on day 29, and compared with pre-treatment, is indicative for the treatment.

A further object of the present invention is the above method or system, wherein a decrease of CD34$^+$CD45$^{dim}$CD133$^-$CD117$^+$ cells as measured after treatment, for example on day 29, and compared with pre-treatment, is indicative for the treatment.

A further object of the present invention is the above method or system, wherein an increase of CD34$^+$CD45$^{dim}$CD133$^+$ cells as measured after treatment, for example on day 29, and compared with pre-treatment, is indicative for the treatment.

A further object of the present invention is the above method or system, wherein a decrease of CD34$^+$CD45$^{dim}$CD117$^+$ cells as measured after treatment, for example on day 8 and on day 29, and compared with pre-treatment, is indicative for the treatment.

A further object of the present invention is the above method or system, wherein a decrease of CD34$^+$CD45$^{dim}$CD133$^+$ cells as measured after treatment, and compared with pre-treatment, is indicative for a response (stable disease).

A further object of the present invention is the above method or system, wherein a decrease of CD34$^+$CD45$^{dim}$CD117$^+$ cells as measured after treatment, and compared with pre-treatment, is indicative for a response (stable disease).

A further object of the present invention is the above method or system, wherein a decrease of CD34$^+$CD45$^{dim}$CD133$^+$CD117$^+$ cells as measured after treatment, and compared with pre-treatment, is indicative for a response (stable disease).

A further object of the present invention is a method or system to determine whether treatment of a patient with the compound 3-Z-[1-(4-(N-((4-methyl-piperazin-1-yl)-methyl-carbonyl)-N-methyl-amino)-anilino)-1-phenyl-methylene]-6-methoxycarbonyl-2-indolinone or a pharmaceutically acceptable salt thereof, preferably the monoethanesulphonate salt form, is effective, comprising the following elements: a patient or doctor requesting such a determination; acquisition of a sample of a biological material from the patient; analysis of the sample using the above described method or system for the monitoring of the treatment of an individual; and communication of the tests results back to the patient or doctor.

The invention also provides a diagnostic kit comprising at least one means for performing a method or system according to the invention. In one aspect, the kit may comprise reagents or materials, such as antibodies or nucleic acids, for monitoring the expression of a biomarker set at the level of mRNA, protein or at the cellular or sample level, and optionally one or more active ingredients for use in testing cells from patient tissue specimens or patient samples, and optionally instructions for use.

A further object of the present invention is the use of a biomarker in a method or system for the monitoring of the treatment of an individual with the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone or a pharmaceutically acceptable salt thereof, preferably the monoethanesulphonate salt form, as described in the foregoing.

LEGEND TO THE FIGURES

FIG. 1: Effect of different compounds on the phospho-tyrosine level of HUVEC cells treated with VEGF. On the abscissa: 1 is the IgG control, untreated with VEGF and unexposed to an active ingredient; 2 is the control untreated with VEGF and unexposed to an active ingredient; 3 is the control treated with VEGF but unexposed to an active ingredient; 4 is treated with VEGF and exposed to 1 µM of compound A1; 5 is treated with VEGF and exposed to 5 µM of compound A1; 6 is treated with VEGF and exposed to 1 µM of compound AG1478; 7 is treated with VEGF and exposed to 5 µM of compound AG 1478; 8 is treated with VEGF and exposed to 1 mM of compound 5FU; 9 is treated with VEGF and exposed to 5 mM of compound 5FU.

Figure 2:
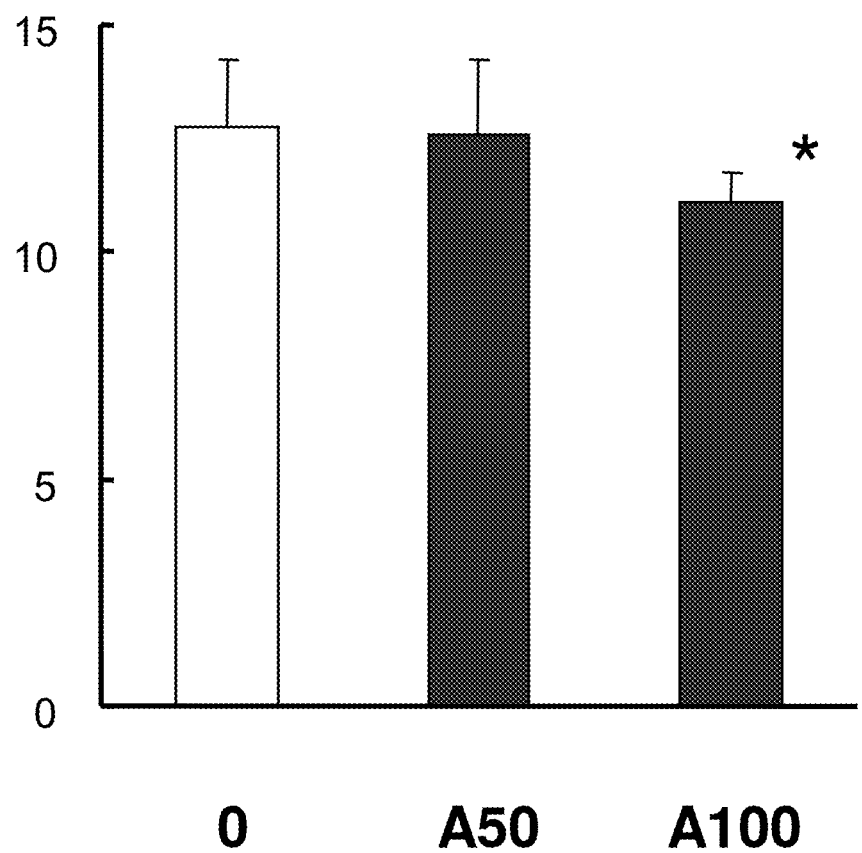

FIG. 2: Phospho-tyrosine levels of VEGFR2$^+$CD45$^{dim}$pY$^+$ leukocyte cells in vivo upon treatment with compound A 1. On the abscissa: 0 represents the untreated control; A50 represents the treatment with 50 mg/kg of compound A 1; A100 represents the treatment with 100 mg/kg of compound A1.

Figure 3:
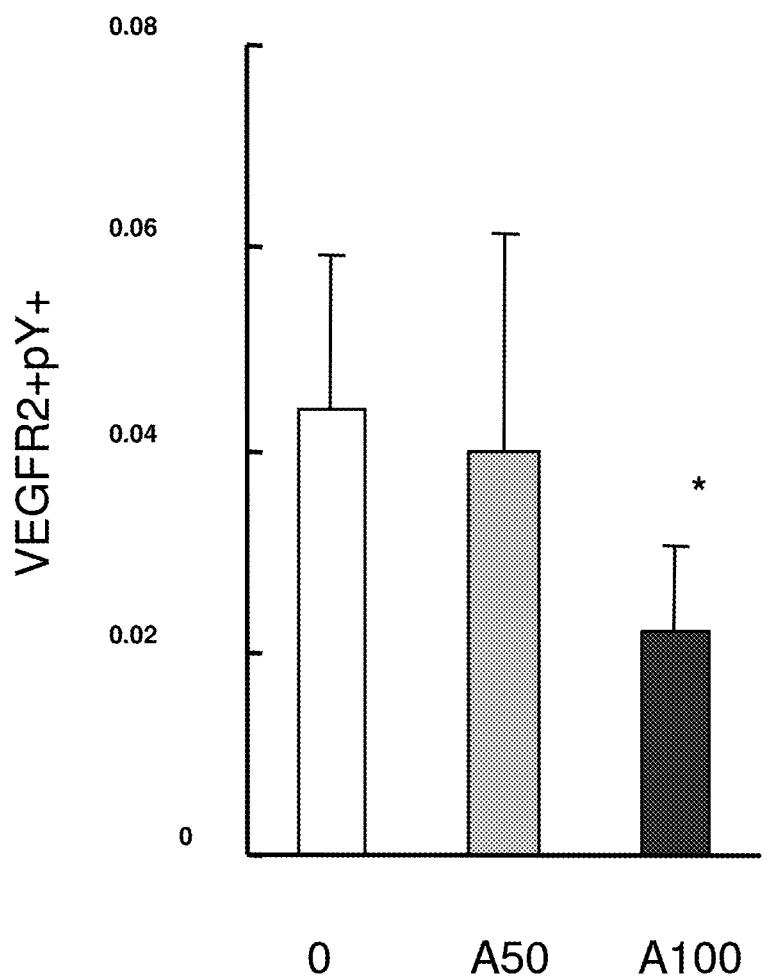

FIG. 3: Flow cytometry of VEGFR2$^+$pY$^+$ cells in murine peripheral blood upon treatment with compound A 1. On the abscissa: 0 represents the untreated control; A50 represents the treatment with 50 mg/kg of compound A1; A100 represents the treatment with 100 mg/kg of compound A1.

Figure 4:
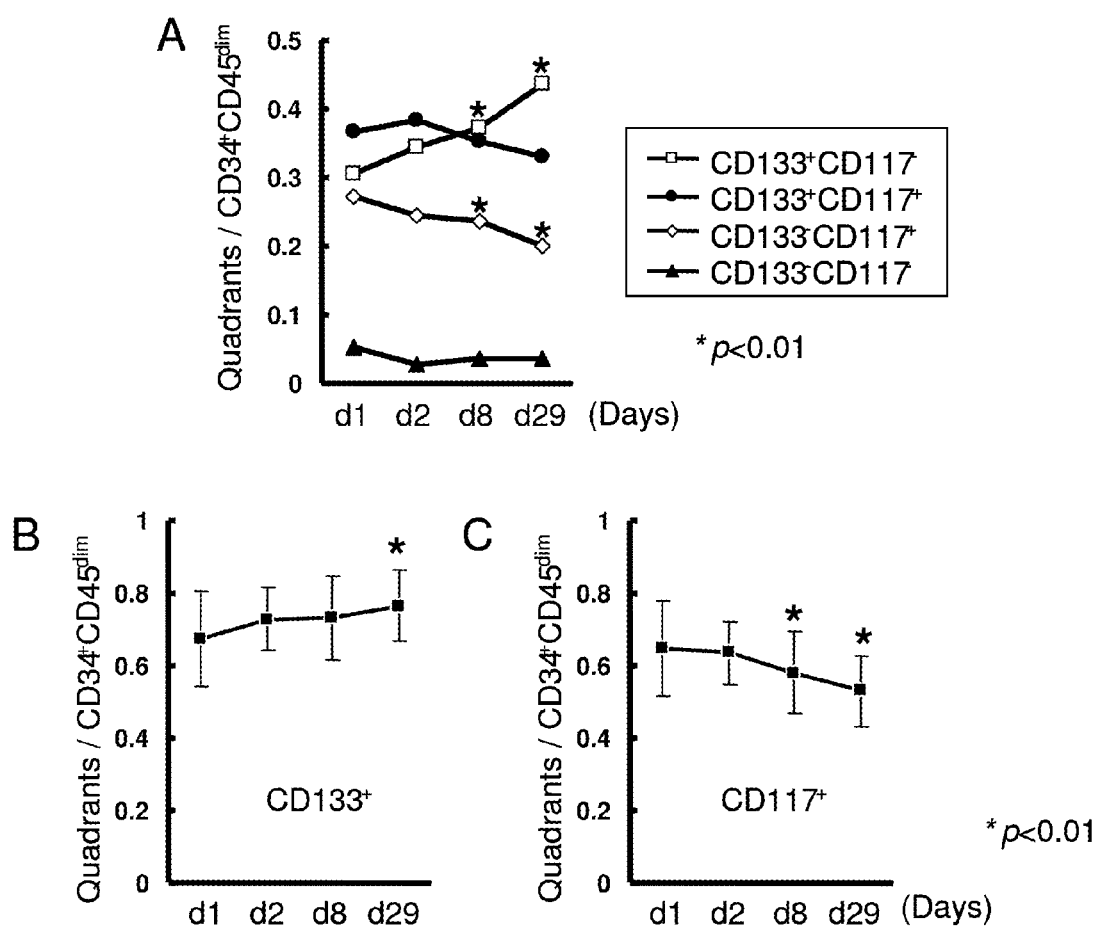

FIG. 4: Percentage (quadrants) of CD34$^+$CD45$^{dim}$CD133+/−CD117+/− cells in the whole blood collected on pre-treatment, and on day 2, day 8 and day 29 after treatment with compound A1.

Figure 5:
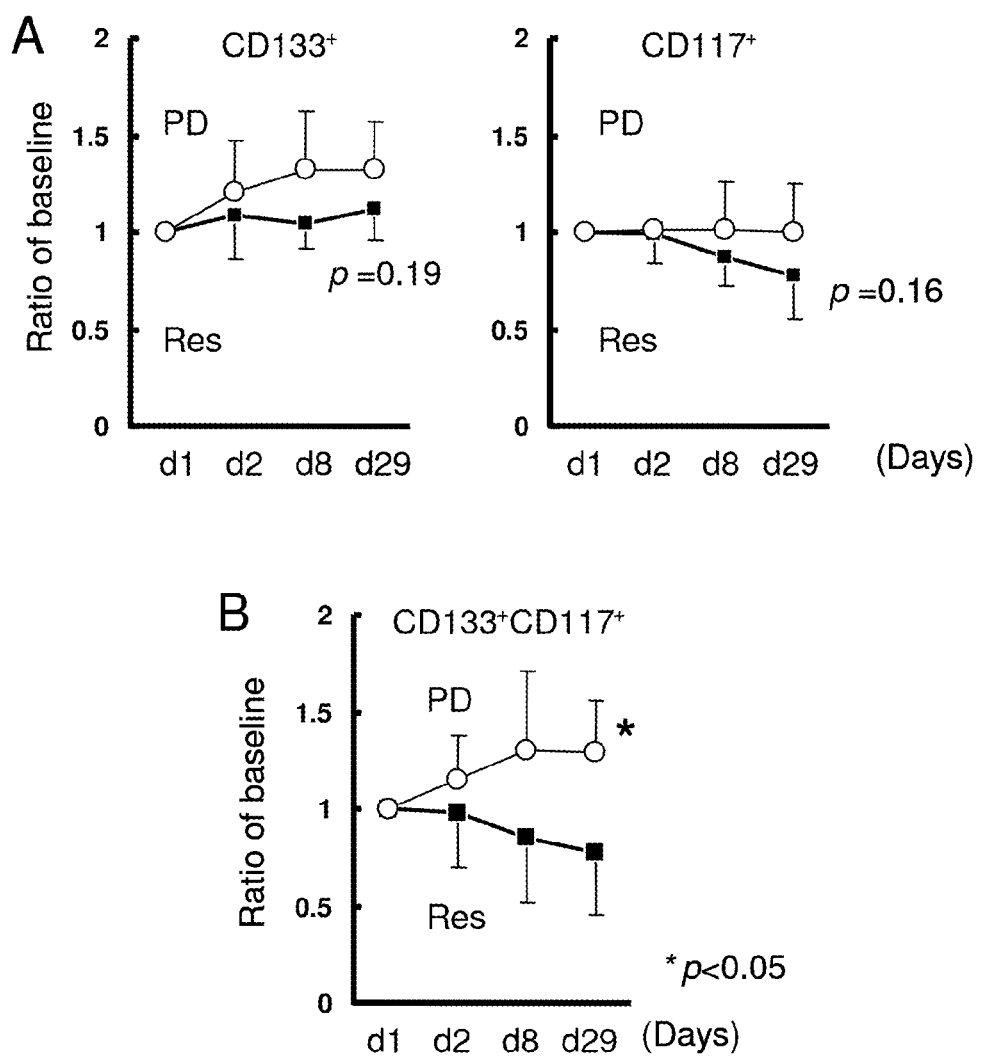

FIG. 5: Ratio of CD34$^+$CD45$^{dim}$CD133+/−CD117+/− cells in the whole blood collected on pre-treatment, and on day 2, day 8 and day 29 after treatment with compound A1, in respondants and in non-respondents.

DETAILED DESCRIPTION OF THE INVENTION

Within the meaning of the present invention, a biomarker is used as an indicator of a biologic state. It is a characteristic that is objectively measured and evaluated as an indicator of normal biologic processes, pathogenic processes, or pharmacologic responses to a therapeutic intervention. This is in line with the definition given by an NIH study group in 1998.

More specifically, a biomarker indicates a change that correlates with the risk or progression of a disease, or with the susceptibility of the disease to a given treatment. Once a proposed biomarker has been validated, it can be used to diagnose disease risk, presence of disease in an individual, or to tailor treatments for the disease in an individual (choices of drug treatment or administration regimes). In evaluating potential drug therapies, a biomarker may be used as a surrogate for a natural endpoint such as survival or irreversible morbidity. If a treatment alters the biomarker, which has a direct connection to improved health, the biomarker serves as a surrogate endpoint for evaluating clinical benefit.

The method or system of the invention can be, for example, an in vitro method wherein the step of measuring in the individual the level of at least one biomarker comprises taking a biological sample from the individual and then measuring the level of the biomarker(s) in the biological sample. The biological sample can comprise, for example, at least one of serum, whole fresh blood, peripheral blood mononuclear cells, frozen whole blood, fresh plasma, frozen plasma, urine, saliva, skin, hair follicle, bone marrow, or tumor tissue.

Within the scope of the present invention, the cluster of differentiation molecules CD34, CD45, CD133 and CD117, are particularly of interest as cell markers of specific cell types.

Hence, the cluster of differentiation (or cluster of designation, often abbreviated as CD) is a protocol used for the identification and investigation of cell surface molecules present on leukocytes. The CD nomenclature was proposed and established in the 1$^{st}$ International Workshop and Conference on Human Leukocyte Differentiation Antigens (HLDA), which was held in Paris in 1982. This system was intended for the classification of the many monoclonal antibodies (mAbs) generated by different laboratories around the world against epitopes on the surface molecules of leukocytes (white blood cells). Since then, its use has expanded to many other cell types, and more than 320 CD unique clusters and subclusters have been identified. The proposed surface molecule is assigned a CD number once two specific monoclonal antibodies (mAb) are shown to bind to the molecule. If the molecule has not been well-characterized, or has only one mAb, it is usually given the provisional indicator "w" (as in "CDw186"). CD molecules can act in numerous ways, often acting as receptors or ligands (the molecule that activates a receptor) important to the cell. A signal cascade is usually initiated, altering the behavior of the cell (cell signaling). Some CD proteins do not play a role in cell signaling, but have other functions, such as cell adhesion. There are approximately 250 different proteins.

The CD system is commonly used as cell markers, allowing cells to be defined based on what molecules are present on their surface. While using one CD molecule to define populations is uncommon (though a few examples exist), combining markers has allowed for cell types with very specific definitions within the immune system.

CD molecules are utilized in cell sorting using various methods including flow cytometry. Cell populations are usually defined using a '+' or a '−' symbol to indicate whether a certain cell fraction expresses or lacks a CD molecule. For example, a "CD34+, CD31−" cell is one that expresses CD34, but not CD31. This CD combination typically corresponds to a stem cell, opposed to a fully-differentiated endothelial cell. The Table 2 below shows CD markers of some hematopoietic stem cells and leukocyte cells.

TABLE 2

| Type of cell | CD markers |
|---|---|
| Stem cells | CD34+, CD31− |
| All leukocyte groups | CD45+ |
| Granulocyte | CD45+, CD15+ |
| Monocyte | CD45+, CD14+ |
| T lymphocyte | CD45+, CD3+ |
| T helper cell | CD45+, CD3+, CD4+ |
| Cytotoxic T cell | CD45+, CD3+, CD8+ |
| B lymphocyte | CD45+, CD19+ or CD45+, CD20+ |
| Thrombocyte | CD45+, CD61+ |

The cluster of differentiation CD34 molecule is a molecule present on certain cells within the human body. Cells expressing CD34 (CD34+ cell) are normally found in the umbilical cord and bone marrow as hematopoeitic cells, endothelial progenitor cells, endothelial cells of blood vessels but not lymphatics (except pleural lymphatics), mast cells, a subpopulation dendritic cells (which are factor XIIIa negative) in the interstitium and around the adnexa of dermis of skin, as well as cells in some soft tissue tumors. It is a cell surface glycoprotein and functions as a cell-cell adhesion factor. It may also mediate the attachment of stem cells to bone marrow extracellular matrix or directly to stromal cells. CD34+ cells may be isolated from blood samples using immunomagnetic or immunofluorescent methods. Antibodies are used to quantify and purify hematopoietic progenitor stem cells for research and for clinical bone marrow transplantation. Thus, because of their CD34+ expression, such cells can be sorted out.

The cluster of differentiation CD45 antigen is a protein which was originally called leukocyte common antigen. The protein encoded by this gene is a member of the protein tyrosine phosphatase (PTP) family. PTPs are known to be signaling molecules that regulate a variety of cellular processes including cell growth, differentiation, mitotic cycle, and oncogenic transformation. This PTP contains an extracellular domain, a single transmembrane segment and two tandem intracytoplasmic catalytic domains, and thus belongs to receptor type PTP. This gene is specifically expressed in hematopoietic cells. This PTP has been shown to be an essential regulator of T- and B-cell antigen receptor signaling. It functions through either direct interaction with components of the antigen receptor complexes, or by activating various Src family kinases required for the antigen receptor signaling. This PTP also suppresses JAK kinases, and thus functions as a regulator of cytokine receptor signaling. Four alternatively spliced transcripts variants of this gene, which encode distinct isoforms, have been reported. It is a type I transmembrane protein which is in various forms present on all differentiated hematopoietic cells except erythrocytes and plasma cells that assists in the activation of those cells (a form of co-stimulation). It is expressed in lymphomas, B-cell chronic lymphocytic leukemia, hairy cell leukemia, and acute nonlymphocytic leukemia.

The cluster of differentiation molecule CD133, also called AC133, is a glycoprotein also known in humans and rodents as Prominin 1 (PROM 1). It is the founding member of pentaspan transmembrane glycoproteins (5-transmembrane, 5-TM), which specifically localizes to cellular protrusions. CD133 is expressed in hematopoietic stem cells, endothelial progenitor cells, glioblastomas, neuronal and glial stem cells and some other cell types.

The cluster of differentiation molecule CD117, also called KIT or C-kit receptor, is a cytokine receptor expressed on the surface of hematopoietic stem cells as well as other cell types.

This receptor binds to stem cell factor (a substance that causes certain types of cells to grow). CD117 is an important cell surface marker used to identify certain types of hematopoietic (blood) progenitors in the bone marrow. Specifically hematopoietic stem cells (HSC), multipotent progenitors (MPP), and common myeloid progenitors (CMP) express high levels of CD117. Common lymphoid progenitors (CLP) expresses low surface levels of CD117. CD117 also identifies the earliest thymocyte progenitors in the thymus. Additionally mast cells, melanocytes in the skin, and interstitial cells of Cajal in the digestive tract express CD117. CD117 is also a marker for mouse prostate stem cells.

As shown in the following and in accordance with the present invention, cells presenting certain cell markers are useful as biomarkers to monitor the treatment of an individual with the active ingredient 3-Z-[1-(4-(N-((4-methyl-piperazin-1-yl)-methylcarbonyl)-N-methyl-amino)-anilino)-1-phenyl-methylene]-6-methoxycarbonyl-2-indolinone or a pharmaceutically acceptable salt thereof, preferably the monoethanesulphonate salt form.

In particular, this includes monitoring the extent of the response, the duration of response, the response rate, the stabilisation rate, the duration of stabilisation, the time to disease progression, the progression free survival or the overall survival, in particular without detriment to the duration of the response, but with fewer and/or less troublesome side-effects.

As stated above the treatments of the present invention as defined herein are of interest for their antiangiogenic and/or vascular permeability effects. Angiogenesis and/or an increase in vascular permeability is present in a wide range of disease states including cancer (including leukaemia. Kaposi's sarcoma, multiple myeloma and lymphoma), diabetes, psoriasis, rheumatoid arthritis, haemangioma, acute and chronic nephropathies, atheroma, arterial restenosis, autoimmune diseases, acute inflammation, asthma, lymphoedema, endometriosis, dysfunctional uterine bleeding, fibrosis, cirrhosis and ocular diseases with retinal vessel proliferation including age-related macular degeneration.

A combination treatment of the present invention as defined herein may be achieved by way of the simultaneous, sequential or separate administration of the individual components of said treatment. A combination treatment as defined herein may be applied as a sole therapy or may involve surgery or radiotherapy or an additional chemotherapeutic or targeted agent in addition to a combination treatment of the invention. Surgery may comprise the step of partial or complete tumour resection, prior to, during or after the administration of the combination treatment as described herein.

Combination treatments of the present invention are expected to be particularly useful in the prophylaxis and treatment of diseases such as cancer and Kaposi's sarcoma. In particular such combination treatments of the invention are expected to slow advantageously the growth of primary and recurrent solid tumours of, for example, the colon, pancreas, brain, bladder, ovary, breast, prostate, lungs and skin. Combination treatments of the present invention are expected to slow advantageously the growth of tumours in lung cancer, including malignant pleural mesothelioma, small cell lung cancer (SCLC) and non-small cell lung cancer (NSCLC), head and neck cancer, oesophageal cancer, stomach cancer, colorectal cancer, gastrointestinal stromal tumor (GIST), pancreatic cancer, hepatocellular cancer, breast cancer, renal cell cancer and urinary tract cancer, prostate cancer, ovarian cancer, brain tumors, sarcomas, skin cancers, and hematologic neoplasias (leukemias, myelodyplasia, myeloma, lymphomas).

More particularly such combination treatments of the invention are expected to inhibit any form of cancer associated with VEGF including leukaemia, multiple myeloma and lymphoma and also, for example, to inhibit the growth of those primary and recurrent solid tumors which are associated with VEGF, especially those tumors which are significantly dependent on VEGF for their growth and spread, including for example, certain tumours of the colon (including rectum), pancreas, brain, kidney, hepatocellular cancer, bladder, ovary, breast, prostate, lung, vulva, skin and particularly malignant pleural mesothelioma and NSCLC. More especially combination treatments of the present invention are expected to slow advantageously the growth of tumours in malignant pleural mesothelioma. More especially combination treatments of the present invention are expected to slow advantageously the growth of tumors in non-small cell lung cancer (NSCLC).

In another aspect of the present invention, the treatment is expected to inhibit the growth of those primary and recurrent solid tumors which are associated with VEGF, especially those tumors which are significantly dependent on VEGF for their growth and spread.

The following studies are intended to illustrate the present invention. The abbreviations used in the description of these studies and throughout the present invention are explained in the following list.

List of Abbreviations

APC Allophycocyanin
BSA Bovine serum albumin
CEC Circulating endothelial mature cell
CEP Circulating endothelial progenitor
Cy5.5 Cyanine 5.5
EGFR Epidermal Growth Factor Receptor
FCM Flow cytometry
FITC Fluoresceinisothiocyanate
FSC Forward Scatter
HepG2 Human hepatocellular liver carcinoma cell line
HUVEC Human Umbilical Vein Endothelial Cells
PBL Peripheral blood leukocyte
PBS Phosphate buffer saline
PD Progressive disease
–PE Labelled with phycoerythrin
PerCP Peridinin chlorophyll protein
PY or
pY Phospho-tyrosine
RES Responder
SSC Side Scatter
TKI Tyrosine kinase inhibitor
VEGFR Vascular endothelial growth factor receptor 2
  Pre-Clinical Study
  The following in vitro and in vivo experiments were performed to evaluate the antitumor activity of compound A1 for hepatocellular carcinoma and to identify new pharmacodynamic biomarkers in blood samples, namely the phosphotyrosine levels of endothelial cells, the number of VEGFR2$^+$CD45$^{dim}$pY$^+$ cells and the number of VEGFR2$^+$pY$^+$ cells.

HUVEC Cells Experiment (FIG. 1)

HUVEC cells were exposed to compound A1 (1 µM and 5 µM), to the EGFR inhibitor AG1478 (1 µM and 5 µM) and to 5FU (5-fluorouracile, 1 mM and 5 mM) for 3 h and 20 ng/ml of VEGF were added for 5 min before cell collection. Collected cells were washed twice by PBS and centrifugation (300 g, 5 min) in 50 µL of staining buffer. After removal of the supernatant by aspiration, cell pellets were lysed in 250 µL of fixation/permeabilization solution and kept for 20 min on ice.

The PY-100 Alexa 488 antibody and phosphatase inhibitor were added. Cells were kept on ice for 30 min in dark, and washed twice by Perm/Wash buffer and lysed again in 500 μL of staining buffer. Then, the cells were examined by flow cytometry (FACS Calibur, BD). The data was obtained from Cell Quest software (BD) and analyzed by WinMDI 2.9 (free software).

Murine Blood Samples for In Vivo Study (FIGS. 2 and 3)

Mice, inoculated HepG2 cells, were randomized for three groups by tumor size and treated with vehicle (control), compound A1 (50 mg/kg, p.o.) or compound A1 (100 mg/kg, p.o.) for 14 days. Mice were sacrificed and whole murine blood samples were collected by aspiration from abdominal aorta or heart. The blood was hemolyzed by an hemolytic agent at room temperature for 10 min. After centrifugation (500 g, 5 min), the cells were washed by 1 mL of staining buffer. The cells were then incubated with 100 μL of staining buffer and 5 μL of VEGFR2-PE antibody for 15 min in the dark. Then, the cells were washed and incubated in 500 μL of Fixation/Permeabilization solution for 20 min and washed by Perm/Wash buffer twice. Then, a mixture of antibodies (PY-100, CD45-PerCP-Cy5.5, 5 μL of each) and phosphatase inhibitor were added and incubated for 30 min in the dark. The cells were washed and analyzed by flow cytometry (FACS Calibur, BD). The data was obtained from Cell Quest software (BD) and analyzed by WinMDI 2.9 (free software).

Antibodies

PY-100 (Phospho-tyrosine) Alexa Fluor 488 Conjugate (Cell Signaling, #9414)

VEGFR2-PE (BD pharm, 555308)

CD45-PerCP-Cy5.5 (BD Pham, 340953)

Alexa Fluor 488 Mouse IgGκ Isotype Control (BD Pham, 557702)

Buffers

BD Cytofix/Cytoperm, Fixation/Permeabilization Kit (Cat.554714)

Staining buffer (Dulbecco's PBS (without $Mg^{2+}$, $Ca2+$) supplemented with 1% heat-inactivated FCS, and 0.09% (w/v)sodium azide, pH adjusted to 7.4-7.6)

10× Lysis buffer ($NH_4Cl$ 82.6 g, $NaHCO_3$ 11.9 g EDTA2Na 0.378 g up to 1 L of $H_2O$, pH adjusted to 7.3)

Results

In the in vitro study, the phospho-tyrosine levels of HUVEC cells were suppressed by compound A 1, but not by AG1478 (the EGFR-TKI) and not by SFU, as can be seen from FIG. 1.

In the in vivo study, compound A1 seems to decrease the number of $VEGFR2^+CD45^{dim}pY^+$ cells, as can be seen from FIG. 2. Furthermore, $VEGFR2^+pY^+$ cells in murine peripheral blood were suppressed by treatment with compound A1, as can be seen from FIG. 3.

Conclusion

To detect the decrease of phospho-tyrosine levels of endothelial cells using flow cytometry is a pharmacodynamic biomarker for the antiangiogenic inhibitor compound A1.

To detect the decrease of $VEGFR2^+CD45^{dim}pY^+$ cells using flow cytometry from blood sample is a pharmacodynamic biomarker for the antiangiogenic inhibitor compound A 1. To detect the decrease of $VEGFR2^+pY^+$ cells using flow cytometry from blood sample is a pharmacodynamic biomarker for antiangiogenic inhibitor compound A1.

Phase I Clinical Study

A further study was performed, namely a Phase I study, to investigate the anti-tumor activity of the compound A1 in patients with advanced solid tumors (ST) and to confirm that CD133- and CD117-positive cells may be useful as biomarkers of the activity of this active ingredient.

Method

Whole blood was collected on pre-treatment (day 1), and on day 2, day 8 and day 29 after treatment. The subpopulation of $CD34^+CD45^{dim}$ peripheral blood cells identified from whole blood was further identified by cell surface markers of CD133 and CD117 using flow cytometry. Whole blood (800 μL) was supplemented with 4.5 mL of 0.2% BSA-PBS and centrifuged for 5 min (1500 rpm). After the removal of the supernatant by aspiration, 4.5 mL of 0.2% BSA-PBS was added and centrifuged. The cell pellet was mixed with 50 μL of human gamma-globulin. Antibodies (CD34-FITC, CD117-PE, CD45-PerCP and CD133-APC) were added and kept for 45 min at 4 C. An hemolytic agent (4.5 mL) was added and incubated for 10 min. After centrifugation (1500 rpm, 5 min), the supernatant was washed twice. Then, 0.2% BSA-PBS (4.5 mL) was added, and the supernatant was removed by centrifugation (1500 rpm, 5 min). The cell pellet was filled up to 800 μL with BSA-PBS and analyzed by flow cytometry. The percentage (quadrants) of $CD34^+$ $CD45^{dim}CD133+/-CD117+/-$ cells were analyzed.

Antibodies

CD34 FITC, BECKMANCOULTER (Cat No. IM1870).
CD117 PE, BECKMANCOULTER (Cat No. IM2732).
CD45 PerCP, BD Biosciences (Cat No. 347464).
CD133 APC, Miltenyi Biotec (Cat No. 130-090-854).

Results

Compound A1 treatment and CD133CD117 cells: Flow cytometry analysis revealed that treatment with compound A1 significantly increased the percentage of $CD34^+CD45^{dim}CD133^+CD117^+$ cells (p<0.001) on day 29 compared with pre-treatment, and conversely decreased that of $CD34^+CD45^{dim}CD133^-CD117^+$ cells (p<0.01, FIG. 4A); $CD34^+CD45^{dim}CD133^+$ cells on day 29 were significantly increased (FIG. 4B); and $CD34^+CD45^{dim}CD117^+$ cells on day Band day 29 were significantly decreased (FIG. 4C). Compound A1 response and CD133CD117 cells: $CD34^+CD45^{dim}CD133^+$ cells and $CD34^+CD45^{dim}CD117^+$ cells tended to decrease in responders (stable disease), but they were not significant (FIG. 5A); $CD34^+CD45^{dim}CD133^+$ $CD117^+$ cells tended to decrease in responders (stable disease) when compared to non-responders after treatment (FIG. 5B), although the data was obtained from very small sample size (RES n=12, PD n=4) and limited evidence.

Conclusion

The pharmacodynamic biomarkers in blood samples for the antiangiogenic inhibitor compound A1 are:

the $CD34^+CD45^{dim}CD133^+CD117^-$ cells;
the $CD34^+CD45^{dim}CD133^-CD117^+$ cells;
the $CD34^+CD45^{dim}CD133^+$ cells; and
the $CD34^+CD45^{dim}CD117^+$ cells.

The predictive biomarker in blood samples for the antiangiogenic inhibitor compound A1 are the $CD34^+CD45^{dim}$ $CD133^+CD117^+$ cells.

Further Embodiments

The diseases which may be treated with the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone or a pharmaceutically acceptable salt thereof, and especially its monoethanesulphonate salt form, when used alone or optionally in combination with further pharmaceutically active ingredients and/or further treatments, such as for example radiotherapy, are diseases involving cell proliferation, migration or apoptosis of myeloma cells, angiogenesis or fibrosis.

In a preferred embodiment, the disease comprises the presence of a tumor.

In a further embodiment, the disease is a progressive tumor.

In a further embodiment, the disease is a fibrotic disease, such as for example idiopatic pulmonary fibrosis.

In a further embodiment, the disease is selected from cancers (including Kaposi's sarcoma, leukaemia, multiple myeloma and lymphoma), diabetes, psoriasis, rheumatoid arthritis, haemangioma, acute and chronic nephropathies, atheroma, arterial restenosis, autoimmune diseases, acute inflammation, asthma, lymphoedema, endometriosis, dysfunctional uterine bleeding, fibrosis, cirrhosis and ocular diseases with retinal vessel proliferation including age-related macular degeneration.

In a further embodiment, the disease is selected from non small cell lung cancer (NSCLC), small-cell lung cancer (SCLC), malignant pleural or peritoneal mesothelioma, head and neck cancer, oesophageal cancer, stomach cancer, colorectal cancer, gastrointestinal stromal tumor (GIST), pancreas cancer, hepatocellular cancer, breast cancer, renal cell cancer, urinary tract cancer, prostate cancer, ovarian cancer, brain tumors, sarcomas, skin cancers and hematologic neoplasias (leukemias, myelodyplasia, myeloma, lymphomas).

Further pharmaceutically acceptable salts of the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone than those already described hereinbefore may, for example, include acid addition salts. Such acid addition salts include, for example, salts with inorganic or organic acids affording pharmaceutically acceptable anions such as with hydrogen halides or with sulphuric or phosphoric acid, or with trifluoroacetic, citric or maleic acid. In addition, pharmaceutically acceptable salts may be formed with an inorganic or organic base which affords a pharmaceutically acceptable cation. Such salts with inorganic or organic bases include for example an alkali metal salt, such as a sodium or potassium salt and an alkaline earth metal salt such as a calcium or magnesium salt.

In accordance with the present invention, the compounds may be formulated using one or more pharmaceutically acceptable excipients or carriers, as suitable. Suitable formulations which may be used within the scope of the present invention have already been described in the literature and in patent applications related to these compounds. These formulations are incorporated herein by reference.

In one embodiment in accordance with the present invention, the formulation for the compound of formula A 1 is a lipid suspension of the active substance comprising preferably a lipid carrier, a thickener and a glidant/solubilizing agent, most preferably in which the lipid carrier is selected from corn oil glycerides, diethylenglycolmonoethylether, ethanol, glycerol, glycofurol, macrogolglycerolcaprylocaprate, macrogolglycerollinoleate, medium chain partial glycerides, medium chain triglycerides, polyethylene glycol 300, polyethylene glycol 400, polyethylene glycol 600, polyoxyl castor oil, polyoxyl hydrogenated castor oil, propylene glycol monocaprylate, propylene glycol monolaurate, refined soybean oil, triacetin, triethyl citrate, or mixtures thereof, the thickener is selected from oleogel forming excipients, such as Colloidal Silica or Bentonit, or lipophilic or amphiphilic excipients of high viscosity, such as polyoxyl hydrogenated castor oil, hydrogenated vegetable oil macrogolglycerol-hydroxystearates, macrogolglycerol-ricinoleate or hard fats, and the glidant/solubilizing agent is selected from lecithin, optionally further comprising one or more macrogolglycerols, preferably selected from macrogolglycerol-hydroxystearate or macrogolglycerol-ricinoleate. The lipid suspension formulation may be prepared by conventional methods of producing formulations known from the literature, i.e. by mixing the ingredients at a pre-determined temperature in a pre-determined order in order to obtain a homogenized suspension.

The above formulation may be preferably incorporated in a pharmaceutical capsule, preferably a soft gelatin capsule, characterised in that the capsule shell comprises e.g. glycerol as plasticizing agent, or a hard gelatin or hydroxypropylmethylcellulose (HPMC) capsule, optionally with a sealing or banding. The capsule pharmaceutical dosage form may be prepared by conventional methods of producing capsules known from the literature. The soft gelatin capsule may be prepared by conventional methods of producing soft gelatin capsules known from the literature, such as for example the "rotary die procedure", described for example in Swarbrick, Boylann, Encyclopedia of pharmaceutical technology, Marcel Dekker, 1990, Vol. 2, pp 269 ff or in Lachmann et al., "The Theory and Practice of Industrial Pharmacy", 2nd Edition, pages 404-419, 1976, or other procedures, such as those described for example in Jimerson R. F. et al., "Soft gelatin capsule update", Drug Dev. Ind. Pharm., Vol. 12, No. 8-9, pp. 1133-44, 1986.

The above defined formulation or the above defined capsule may be used in a dosage range of from 0.1 mg to 20 mg of active substance/kg body weight, preferably 0.5 mg to 4 mg active substance/kg body weight.

The above defined capsules may be packaged in a suitable glass container or flexible plastic container, or in an aluminum pouch or double poly bag.

The dosages and schedules may vary according to the particular disease state and the overall condition of the patient. Dosages and schedules may also vary if, in addition to a treatment with compound A of the present invention or a pharmaceutically acceptable salt thereof, one or more additional chemotherapeutic agents is/are used. Scheduling can be determined by the practitioner who is treating any particular patient.

Radiotherapy may be administered according to the known practices in clinical radiotherapy. The dosages of ionising radiation will be those known for use in clinical radiotherapy. The radiation therapy used will include for example the use of γ-rays, X-rays, and/or the directed delivery of radiation from radioisotopes. Other forms of DNA damaging factors are also included in the present invention such as microwaves and UV-irradiation. For example X-rays may be dosed in daily doses of 1.8-2.0 Gy, 5 days a week for 5-6 weeks. Normally a total fractionated dose will lie in the range 45-60 Gy. Single larger doses, for example 5-10 Gy may be administered as part of a course of radiotherapy. Single doses may be administered intraoperatively. Hyperfractionated radiotherapy may be used whereby small doses of X-rays are administered regularly over a period of time, for example 0.1 Gy per hour over a number of days. Dosage ranges for radioisotopes vary widely, and depend on the half-life of the isotope, the strength and type of radiation emitted, and on the uptake by cells.

The size of the dose of each therapy which is required for the therapeutic or prophylactic treatment of a particular disease state will necessarily be varied depending on the host treated, the route of administration and the severity of the illness being treated. Accordingly the optimum dosage may be determined by the practitioner who is treating any particular patient. For example, it may be necessary or desirable to reduce the above-mentioned doses of the components of the combination treatments in order to reduce toxicity.

What is claimed is:

1. A method for the monitoring of the treatment of an individual with the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone or a pharmaceutically acceptable salt thereof, said method comprising
determining whether a sample of blood from said individual comprises at least one pharmacodynamic biomarker in an amount that is indicative for said treatment, wherein said biomarker is the number of biomarker cells selected from the group consisting of $CD34^+CD45^{dim}CD133^+CD117^-$ cells, $CD34^+CD45^{dim}CD133^-CD117^+$ cells, $CD34^+CD45^{dim}CD133^+$ cells, $CD34^+CD45^{dim}CD117^+$ cells and $CD34^+CD45^{dim}CD133^+CD117^+$ cells,
wherein determining whether the sample comprises the number of said pharmacodynamic biomarker cells that is indicative for said treatment comprises isolating said cells from the sample and measuring the number of said cells,
wherein
when the biomarker is $CD34^+CD45^{dim}CD133^+CD117^-$ cells or $CD34^+CD45^{dim}CD133^+$ cells, an increase in the number of cells in a treated patient when compared with pre-treatment is indicative of a pharmacological response to said treatment;
when the biomarker is $CD34^+CD45^{dim}CD133^+CD117^+$ cells or $CD34^+CD45^{dim}CD117^+$ cells, a decrease in the number of cells in a treated patient when compared with pre-treatment is indicative of a pharmacological response to said treatment; and
when the biomarker is $CD34^+CD45^{dim}CD133^+CD117^+$ cells, a decrease in the number of cells after treatment is a predictive biomarker indicative of stable disease, and
wherein an indication of pharmacological response or stable disease is correlated with less risk from or lack of progression of the disease, or that the disease is susceptible to the given treatment.

2. The method in accordance with claim 1, wherein the compound is the monoethanesulphonate salt form of 3-Z-[1-(4-(N-((4-methyl-piperazin-1-yl)-methylcarbonyl)-N-methyl-amino)-anilino)-1-phenyl-methylene]-6-methoxycarbonyl-2-indolinone.

3. The method in accordance with claim 1, wherein the biomarker indicates a change in the amount of specific cells that correlates with the risk or progression of a disease or with the susceptibility of the disease to a given treatment.

4. The method in accordance with claim 1, wherein said biomarker is selected from the number of $CD34^+CD45^{dim}CD133^+CD117^-$ cells, the number of $CD34^+CD45^{dim}CD133^-CD117^+$ cells, the number of $CD34^+CD45^{dim}CD133^+$ cells and the number of $CD34^+CD45^{dim}CD117^+$ cells.

5. A method of claim 4, wherein the level of biomarker in multiple samples from the patient obtained at different times after initiation of treatment are further indicative of whether continuation of treatment is appropriate.

6. The method in accordance with claim 1, wherein said biomarker is the number of $CD34^+CD45^{dim}CD133^+CD117^+$ cells.

7. A method of claim 1, wherein determining whether a sample from said individual comprises a pharmacodynamic biomarker is an immunomagnetic or immunofluorescent assay method.

8. A method of claim 7, wherein the assay method is flow cytometry.

9. A method to determine whether treatment of a patient with the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone or a pharmaceutically acceptable salt thereof, is effective, comprising: a patient or doctor requesting such a determination; acquisition of a blood sample from the patient; analysis of the sample using a method comprising determining whether a sample from said individual comprises at least one biomarker in an amount that is indicative for said treatment; and communication of the tests results back to the patient or doctor,
wherein said biomarker is the number of biomarker cells selected from the group consisting of $CD34^+CD45^{dim}CD133^+CD117^-$ cells, $CD34^+CD45^{dim}CD133^-CD117^+$ cells, $CD34^+CD45^{dim}CD133^+$ cells, $CD34^+CD45^{dim}CD117^+$ cells and $CD34^+CD45^{dim}CD133^+CD117^+$ cells,
wherein determining whether the sample comprises the number of said biomarker cells that is indicative for said treatment comprises isolating said cells from the sample and measuring the amount of said cells,
wherein
when the biomarker is $CD34^+CD45^{dim}CD133^+CD117^-$ cells or $CD34^+CD45^{dim}CD133^+$ cells, an increase in the number of cells in a treated patient when compared with pre-treatment is indicative of an effective pharmacological response to said treatment;
when the biomarker is $CD34^+CD45^{dim}CD133^+CD117^+$ cells or $CD34^+CD45^{dim}CD117^+$ cells, a decrease in the number of cells in a treated patient when compared with pre-treatment is indicative of an effective pharmacological response to said treatment; and
when the biomarker is $CD34^+CD45^{dim}CD133^+CD117^+$ cells, a decrease in the number of cells in responders when compared to non-responders after treatment is indicative of the treatment being effective to maintain stable disease.

* * * * *

UNITED STATES PATENT AND TRADEMARK OFFICE
CERTIFICATE OF CORRECTION

| | | |
|---|---|---|
| PATENT NO. | : 8,802,384 B2 | Page 1 of 1 |
| APPLICATION NO. | : 12/720663 | |
| DATED | : August 12, 2014 | |
| INVENTOR(S) | : Arao et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 596 days.

Signed and Sealed this
Twenty-second Day of September, 2015

Michelle K. Lee
*Director of the United States Patent and Trademark Office*